| United States Patent [19] | [11] | 4,143,125 |
|---|---|---|
| Dyroff et al. | [45] | Mar. 6, 1979 |

[54] CALCULUS-INHIBITING COMPOSITIONS AND METHOD

[75] Inventors: David R. Dyroff, Creve Coeur, Mo.; Walton F. Suchanek, Jr., Belleville, Ill.

[73] Assignee: Monsanto Company, St. Louis, Mo.

[21] Appl. No.: 754,371

[22] Filed: Dec. 27, 1976

[51] Int. Cl.$^2$ .......................... A61K 9/68; A61K 7/16
[52] U.S. Cl. ...................................... 424/48; 424/49; 424/317
[58] Field of Search ...................................... 424/48–58, 424/317

[56] References Cited

U.S. PATENT DOCUMENTS

| Re. 28,325 | 1/1975 | White | 210/58 |
|---|---|---|---|
| 3,542,917 | 11/1970 | Schwartz | 424/49 |
| 3,671,626 | 6/1972 | Felger | 424/49 |
| 3,920,837 | 11/1975 | Schmidt-Dunker et al. | 424/49 X |

FOREIGN PATENT DOCUMENTS

| 2411383 | 9/1974 | Fed. Rep. of Germany. |
| 1376730 | 12/1974 | United Kingdom. |

Primary Examiner—Shep K. Rose
Attorney, Agent, or Firm—S. M. Tarter; E. P. Grattan; F. D. Shearin

[57] ABSTRACT

Oral compositions such as mouth washes, toothpastes, other oral hygiene products, foods, beverages, chewing gums and the like containing certain alkylenedioxybis-(alkyl-propanedioic acid) compounds inhibit the formation of dental calculus.

17 Claims, No Drawings

CALCULUS-INHIBITING COMPOSITIONS AND METHOD

BACKGROUND OF THE INVENTION

The field of this invention is "oral compositions" which term herein means products intended for introduction into the oral cavity in such a manner as to contact exposed dental surfaces therein. Examples of such products are animal foods and beverages, chewing gums and oral hygiene products including mouth washes, prophylaxis pastes, topical solutions and dentifrices such as toothpastes, tooth powders, dental creams and the like.

Dental calculus, or tartar as it is sometimes called, is a deposit which forms on the surfaces of teeth predominantly at or near the gingival margin. Supragingival calculus appears most heavily in areas near the orifices of the salivary ducts. Mature calculus contains an inorganic portion which is largely calcium phosphate arranged in a hydroxyapatite crystal lattice structure similar to that occurring in bone, enamel or dentine. An organic portion is typically also present consisting of desquamated epithelial cells, salivary sediment, food debris, various types of microorganisms, etc.

As calculus develops, it becomes visibly white or yellowish unless stained or discolored by some extraneous substance. In addition to being undesirable from an esthetic standpoint, mature calculus deposits are sources of irritation of the gingiva and thereby a contributing factor to gingivitis and other diseases of the supporting structures of the teeth, the irritation decreasing the resistance of tissues to endogenous and exogenous organisms.

Periodic mechanical removal of this material by a dentist or dental technician is routine dental office procedure. There have also been proposed a number of chemical agents for calculus removal. For example, alkali metal and ammonium diglycolates and diglycolates of organic bases such as urea, guanidine or ethanolamine are suggested for that use in U.K. Pat. No. 995,330 issued June 16, 1965 to R. A. Oetker. In French Pat. No. 2,108,827 published May 26, 1972 it is said that the calcium ion-sequestering capability of sodium gluconate can be used for removal of tartar from the teeth. In U.S. Pat. No. 1,516,206 issued Nov. 18, 1924 to C. Pfanstiehl it is said that a tartar solvent effect is provided by use of an aqueous solution of a lactone or anhydride of a weak organic hydroxy acid, e.g., galactonic acid, together with a weak organic acid such as maleic or citric acid, and it is taught in U.S. Pat. No. 3,429,963 issued Feb. 25, 1969 to L. Shedlovsky that dental calculus can be removed by use of dental preparations containing a hydrolyzed copolymer of ethylene and maleic anhydride having an average molecular weight of at least about 1500.

In some instances, chemical agents have been said to be capable of retarding calculus formation. For example, in the aforementioned U.S. Pat. No. 3,429,963 it is disclosed that a reduction in calculus formation was observed in rats when the drinking water given to the rats contained 1% of a hydrolyzed copolymer of ethylene and maleic anhydride. Another polymer, i.e., a polyester of a polycarboxylic acid having three or more carboxyl groups and a polyalkylene ether having at least two hydroxyl groups, is described as a calculus retarding agent in U.S. Pat. No. 3,542,917 issued Nov. 24, 1970 to A. M. Schwartz et al. In U.S. Pat. No. 3,920,837 issued Nov. 18, 1975 to M. Schmidt-Dunker et al. it is said that tartar formation can be reduced by cyclohexanehexacarboxylic acid or its water-soluble salts, and in U.K. Pat. Nos. 1,373,001 and 1,373,003 issued Nov. 6, 1974 to R. Hoyles et al. it is said that calculus can be reduced by use of a dentifrice containing a sparingly water-soluble zinc salt, e.g., zinc citrate. Various phosphorous compounds such as, e.g., ethane-1-hydroxy-1,1-diphosphonic acid (hereinafter EHDP) have also been proposed for such use in U.S. Pat. No. 3,488,419 issued Jan. 6, 1970 to H. W. McCune et al.

Some chemical agents heretofore proposed for calculus removal or retardation contain functional groups of uncertain effect on animals in terms of toxicity, side effects, etc. Certain other kinds of compounds containing only carbon, hydrogen, oxygen and possibly pharmaceutically acceptable cations are believed essentially free from such uncertainty and therefore preferable for use in oral compositions. Also desirable for present purposes are compounds of relatively simple structure and low molecular weight, as well as compounds which can be prepared without resort to a polymerization process. Accordingly, oral compositions containing compounds which meet those criteria and substantially inhibit dental calculus formation are highly desirable, and it is an object of this invention to provide such compositions. Another object is a method for inhibiting dental calculus formation by use of such compositions. Other objects will be apparent from the following disclosure in which percentages are by weight except where otherwise noted.

SUMMARY OF THE INVENTION

This invention provides an oral composition effective in inhibiting formation of dental calculus, said composition comprising (1) an alkylenedioxybis(alkylpropanedioic acid) compound selected from the group consisting of acids having the structural formula:

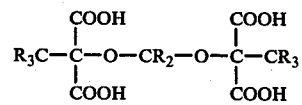

wherein R is hydrogen or lower alkyl, and pharmaceutically acceptable salts of said acids and (2) a carrier suitable for use in the oral cavity, said compound being present in said composition in amount and concentration sufficient to substantially inhibit formation of dental calculus. Also provided by this invention is a method for inhibiting formation of dental calculus by introducing an oral composition of the kind just described into an oral cavity containing exposed dental surfaces. In preferred embodiments, the oral composition in which such a calculus-inhibiting compound is employed in accordance with this invention is selected from the group consisting of oral hygiene products, foods, beverages and chewing gums.

DESCRIPTION OF PREFERRED EMBODIMENTS

In the foregoing formula each R can be the same as or different from any other R in that formula. Also as used herein, "lower alkyl" means $C_1$-$C_4$ alkyl which can be branched (e.g., isopropyl, isobutyl or tert-butyl) or cyclic (cyclopropyl or cyclobutyl) or straight-chain (methyl, ethyl, n-propyl or n-butyl). In many embodiments of the invention it is preferred that R in the foregoing formula is hydrogen or normal alkyl, and in some of those embodiments it is even more preferred that R is hydrogen, methyl or ethyl. It is preferred that at least one R in the —$CR_2$— radical in that formula is hydrogen, and it is generally even more preferred that each R in that —$CR_2$— radical is hydrogen. In some embodiments it is preferred that at least 2 R's in each of the two —$CR_3$ groups in that formula are hydrogen, and it is also typically preferred that the total number of carbon atoms in each of said —$CR_3$ groups is not greater than 7. In an embodiment of particular preference, each R in the foregoing formula is hydrogen. Each of these embodiments is preferable on the basis of relatively low molecular weight. On the other hand, some compounds similar to those expressly included in that formula but wherein at least one of the R's in that formula contains more than four carbon atoms may similarly inhibit calculus formation when used in suitable oral compositions and in such cases should be regarded as equivalents of said alkylenedioxybis(alkyl-propanedioic acid) compounds for purposes of this invention.

The compound represented by the foregoing formula when R is hydrogen is herein designated 2,2'-dimethyl-2,2'-(methylenedioxy)-bis(propanedioic acid) (hereinafter for convenience called DMBPDA). The tetrasodium salt of that acid can be prepared by contacting an appropriate diester of methyl tartronic acid, e.g., a di(-lower alkyl)ester such as diethyl methyl tartronate, with a base strong enough to deprotonate the hydroxy group of that diester (e.g., metallic sodium or potassium or sodium or potassium hydride, tert-butoxide or amide) and form a conjugate base in which the deprotonated oxygen atom of the diester is associated with a cation furnished by that base (e.g., a sodium or potassium ion), then reacting that conjugate base with a dihalomethane (e.g., dibromomethane) in a two-to-one molar ratio to form the tetraester of DMBPDA, and then saponifying that tetraester with sodium hydroxide.

Sodium salts of acids represented by the foregoing formula when at least one R in a —$CR_3$ radical in that formula is lower alkyl can be made by procedure analogous to that just described but in which the methyl tartronate diester is at least partly replaced with a tartronic acid diester having on its hydroxylated carbon atom an alkyl substituent that is appropriately larger than methyl, e.g., ethyl, n-propyl, n-butyl, isopropyl, isobutyl, tert-butyl, etc. Sodium salts of acids represented by that formula when at least one R in the $CR_2$ radical is lower alkyl can be made by procedure analogous to that just described but in which the dihalomethane is replaced with a dihaloalkane having two halogen atoms directly attached to the same carbon atom of an alkylene radical that is appropriately larger than methylene, e.g., a dihaloalkane such as 1,1-diiodoethane, 1,1-dibromopropane, 2,2-dibromopropane, 2,2-dibromobutane, 2-methyl-3,3-dibromopentane, 2,2-dimethyl-3,3-dibromo-5-methylhexane, etc.

The conversion of hydroxylated compounds to their conjugate base forms is known in the art. The reaction is conveniently carried out between 0° and 115° C. in any solvent for the hydroxylated compound not adversely reactive with the strong base. Examples of suitable solvents include tetrahydrofuran, dimethylsulfoxide, dimethylformamide, ethylether, 1,2-dimethoxyethane, bis(2-methoxyethyl)ether and the like. In those instances where the tartronate reactant is a liquid, an excess thereof may be employed as the solvent. Mixed solvents can be used, if desired. More detailed discussion of the conversion of alcohols to conjugate bases is found in such references as Morrison and Boyd, *Organic Chemistry*, 3rd edition, Allyn and Bacon, Inc. (1973) pp. 526, 527; Feuer and Hooz, *The Chemistry of the Ether Linkage*, edited by Patai, Interscience Publishers (1967), Chapter 10, p. 447; and Schmidt and Bayer, *Methoden Der Organischen Chemie* (Houben-Weyl) Band VI/2, Georg Thieme Verlag, (1963) Sauerstoff Vergindungen 1, Teil 2 and bibliographies provided in the foregoing references.

Reactions of such conjugate bases with haloalkanes to form ether linkage containing compounds are also known in the art. In the procedure described hereinbefore it is usually desirable to use a diiodoalkane or, generally even more preferably, a dibromoalkane. Either may be added to the alkyl tartronate diester as such or produced in situ, e.g. by using a mixture of sodium iodide or bromide and an appropriate dichloroalkane such as, for example, dichloromethane, 1,1-dichloroethane, 1,1-dichloro-n-propane, 2,2-dichloropropane, 2,2-dichloro-n-butane or the like. A reaction temperature between —20° and 100° C. is usually satisfactory and an elevated or atmospheric pressure can be used.

Any of the aforementioned alkylenedioxybis(alkyl-propanedioic acid) salts can be converted to the corresponding acid (e.g. DMBPDA) by treatment with a strong acid, e.g. HCl, $H_2SO_4$ or a strongly acidic ion exchange resin. Other metal salts of the resulting acids can be prepared by neutralization with the appropriate metal hydroxide, e.g., an alkali metal hydroxide such as potassium hydroxide. The corresponding ammonium, mono- or di($C_1$-$C_3$ alkyl)ammonium or mono or di($C_1$-$C_3$ alkanol)ammonium salts can be prepared by treating such acids with ammonia, an appropriate alkylamine or alkanolamine or hydroxide thereof in accordance with procedures well known in the art.

In the oral compositions of this invention, the proportions in which the alkylenedioxybis(alkyl-propanedioic acid) compounds are present as acids and/or partially-substituted or fully-substituted salts thereof are dependent on the pH of the composition. That pH is normally between about 4 and about 11, although in some instances it may be higher or lower than that range. Below about pH 4 there is a greater danger of damage to dental enamel despite the relative safety of the aforementioned acid or its salts. Above about pH 11, greater difficulty is encountered in formulating products having satisfactory flavor and mildness. A preferred pH range is from about 6 to about 10. In many embodiments, the pharmaceutically acceptable salts employed are preferably water-soluble salts such as, e.g., sodium, potassium or ammonium salts, to facilitate their dissolution in saliva.

As aforesaid, some embodiments of this invention are oral hygiene products such as dentifrices, mouth washes, prophylaxis pastes and topical solutions. A dentifrice, especially toothpaste, containing a calculus-inhibiting amount of an acid represented by the foregoing formula and/or a pharmaceutically acceptable salt thereof is a preferred embodiment of this invention. A mouth wash containing such an acid and/or salt is another preferred embodiment. Except for inclusion of an alkylenedioxybis(alkyl-propanedioic acid) compound as aforesaid, many formulations of such products are well known in the art. For example, typical formulations of toothpastes and mouth washes compatible with calculus-inhibiting compounds of the kind employed in accordance with this invention are described in U.S.

Pat. Nos. 3,639,569 issued Feb. 1, 1972 to R. F. Medcalf, Jr., 3,544,678 issued Dec. 1, 1970 to W. J. Griebstein, 3,678,154 issued July 18, 1972 to J. S. Widder et al. and 3,959,458 issued May 25, 1976 to F. O. Agricola et al., the disclosures of which are incorporated herein by reference.

Under conditions of normal use, the oral compositions of this invention are pharmaceutically acceptable, i.e., capable of introduction into the oral cavity without significant adverse effect on tooth structure or other injury to health. Subject to the limits of such acceptability, the calculus-inhibiting amounts and concentrations of the alkylenedioxybis(alkyl-propanedioic acid) compounds can be varied widely in the oral compositions of this invention. Such amounts and concentrations are also readily definable for each kind of oral composition by formulators skilled in the art. Generally, concentrations from 0.01% to about 10% are preferred. Oral compositions which in ordinary usage may be accidentally or intentionally ingested can contain relatively low but still highly effective concentrations. Of course, any such ingested composition should be physiologically (i.e., digestively) acceptable. Thus, a mouth wash in accordance with this invention typically contains between about 0.1 and about 3% of the aforementioned calculus-inhibiting compound. Dentifrice compositions, topical solutions and prophylaxis pastes, the last normally administered professionally, may desirably contain up to about 10% or even more thereof but usually contain between about 0.1 and about 5% and even more typically between about 1 and about 2% thereof.

While it is not intended that this invention be limited to any particular theory of operation, it appears that the alkylenedioxybis(alkyl-propanedioic acid) compounds inhibit calculus formation by interfering with the conversion of dissolved calcium phosphate in saliva to crystalline deposits in the nature of calcium hydroxyapatite. Hence the compositions of this invention preferably do not contain soluble polyvalent cations in an amount likely to deplete the crystal growth inhibiting capacity of those compounds to the extent that their calculus formation inhibiting activity would be essentially neutralized.

The following specific examples are illustrative only and do not imply any limitations on the scope of the invention.

EXAMPLES I-V

A. Evaluations of Calculus Inhibition

Evaluations of the effectiveness of compounds employed in accordance with this invention to inhibit calculus formation were carried out fundamentally as described in "A Method and Apparatus for Studying In Vitro Calculus" by S. Yankelowitz et al. of the Colgate-Palmolive Co., Journal of Dental Research 44 (No. 4), 648-53 (1965). In accordance with that method, now well known in the art, simulated oral calculus deposits are caused to be formed on glass slides by mechanically rotating the slides edgewise and vertically at 0.5 rpm in such a way that each slide passes alternately through a small sample of whole human saliva containing 0.1% of added monocalcium phosphate and then through a forced draft of air which at least partially dries each slide before it passes again through that saliva sample. As stated in the journal article just mentioned, the resulting calculus deposits have been found similar to oral calculus deposits in both composition and X-ray diffraction pattern.

In the present evaluations, 150 mls of stimulated saliva were collected over a 3-day period (50 ml/day) from a donor whose saliva had been previously found to have a substantial tendency toward calculus formation. The collected saliva was also of a type in which, under the conditions of this test, calculus formation is inhibited by EHDP substantially more than by water substituted for the EHDP in a comparative test run. Each 50 ml portion of the saliva was kept frozen until ready for use. At that time the combined 150 ml sample was neutralized to pH 7± .05 after addition of the 0.1% of monocalcium phosphate, thoroughly stirred and then divided into 25 ml aliquots. To one aliquot was added 1 ml of a 0.1 M solution of the tetrasodium salt of DMBPDA, and to a second aliquot was added 1 ml of a 0.1 M solution of the prior art anti-calculus compound EHDP, each of those solutions having been previously neutralized with NaOH or $H_2SO_4$. To a third aliquot was added 1 ml of distilled water.

For comparative test purposes, the three aliquots were then placed in identical side-by-side trough-like containers in an oven equipped with apparatus adapted to rotate a separate set of three 22 × 40 mm glass slides (spaced about 120° apart in relation to the rotating shaft on which they were mounted) through each of the saliva containers and to maintain a steady horizontal flow of air against the slides and perpendicular to the axis of their rotation. All slides used were essentially identical and mounted on the shaft such that the same portion (24 mm) of the length of each slide passed through the appropriate saliva sample.

In the oven just described, the calculus formation test was continued for 20 consecutive hours with the interior of the oven maintained at 37± 1° C. and a relative humidity between 76 and 78%. The saliva samples were then removed from the oven, after which rotation of the slides in the flow of air was continued for an additional hour before removal of the slides from the oven. The weight of each slide and any deposit remaining thereon was then compared with the weight of the slide prior to its use in this test, and visual appraisals of the deposits were made using photographs taken of each slide under identical conditions to further eliminate variables from those appraisals. Results were recorded separately for each of the three slides in each set and then averaged. Thereafter, the entire procedure was repeated using saliva from a different donor and the results of the two runs were averaged to provide the results reported hereinafter.

In these tests it was found that the weights of simulated calculus on the slides that had been exposed to the salivas containing the tetrasodium salt of DMBPDA averaged 0.32 mg, those on the slides used in the comparative runs with EHDP averaged 0.30 mg, and those on the slides used in the comparative runs with water averaged 0.67 mg. Thus in the runs using the DMBPDA salt, formation of the simulated calculus averaged 52% less than in the comparative runs using water, while in the runs using EHDP it averaged 55% less than in the comparative runs using water. In the visual appraisals, the amounts of opaque material deposited on the slides that had been exposed to the salivas containing the DMBPDA salt were judged to be, on average, about the same as those on the slides used in the comparative runs with EHDP and much less than half as great as those on the slides used in the comparative runs with water.

B. Preparation of Oral Compositions

The compound tested in Part A of these examples, the corresponding acid and other pharmaceutically acceptable salts of that acid are useful for inhibition of dental calculus formation when incorporated in compatible carriers or vehicles of any of the usual types. The following are examples of mouth wash compositions comprising at least one of such compounds.

|  | Examples | | | |
| --- | --- | --- | --- | --- |
|  | I | II | III | IV |
| Component | Parts by weight | | | |
| Glycerine | 10.0 | 10.0 | 10.0 | 10.0 |
| Ethyl alcohol | 16.5 | 16.5 | 16.5 | 16.5 |
| Water | 67.172 | 67.172 | 67.172 | 70.192 |
| Tween 80[1] | .12 | .12 | .12 | .12 |
| Saccharin | .045 | .045 | .045 | .02 |
| Sodium Cyclamate | 0.75 | 0.75 | 0.75 | .04 |
| Flavor | .088 | .088 | .088 | .088 |
| Salt of DMBPDA | [2]3.0 | [3]4.0 | [4]2.0 | [5]1.8 |
| pH[6] | 7.0 | 7.0 | 8.5 | 10.0 |

[1]Polyoxyethylene (20 moles of ethylene oxide) sorbitan monoocleate - a nonionic emulsifier supplied at Atlas Powder Co.
[2]Tetraammonium salt.
[3]Tetra(triethanolammonium) salt.
[4]Tetrasodium salt.
[5]Tetrapotassium salt.
[6]Adjusted to value indicated with NaOH or $H_2SO_4$.

The following is an example of a toothpaste composition comprising at least one of such compounds.

|  | Example V |
| --- | --- |
| Component | Parts by weight |
| Water | 31.58 |
| Sorbitol | 6.25 |
| Saccharin | 0.12 |
| Calcium pyrophosphate[1] | 39.00 |
| Glycerine | 18.00 |
| Sodium alkyl (coconut) sulfate | 0.40 |
| Sodium coconut monoglyceride sulfonate | 0.75 |
| Sodium carboxymethyl cellulose | 1.15 |
| Magnesium aluminum silicates | 0.40 |
| Flavoring | 0.85 |
| DMBPDA | 1.00 |
| pH[2] | 5.90 |

[1]Prepared in accordance with U.S. Patent 3,112,247 granted November 26, 1963.
[2]Adjusted to indicated pH with sodium hydroxide.

Other examples of toothpaste compositions comprising at least one of said alkylenedioxybis(alkyl-propanedioic acid) compounds are substantially identical to the toothpaste composition above except for substitution of the corresponding potassium or ammonium salt of DMBPDA or the sodium, potassium or ammonium salt of 2,2'-diethyl-2,2'-(methylenedioxy)-bis(-propanedioic acid) or 2,2'-diisopropyl-2,2'-(methylenedioxy)-bis(propanedioic acid).

Additional examples of oral compositions comprising at least one of such compounds include other mouth washes and toothpastes, tooth powders, dental creams and prophylaxis pastes for use by a dentist or dental technician in polishing of teeth after removal of calculus deposits. Examples of such compositions, except for inclusion of a calculus-inhibiting compound of the kind used in accordance with the present invention, are described in the aforementioned U.S. Pat. Nos. 3,544,678, 3,639,569, 3,678,154 and 3,959,458. Typically, toothpastes are aqueous compositions containing a polishing agent, a surfactant, a binder, a humectant, a preservative, flavoring and sweetening agents and optionally therapeutic agents. Mouth washes typically contain water, ethanol, flavoring, sweetening and coloring agents and optionally a surfactant. Other examples of oral compositions comprising at least one of the compounds used in accordance with this invention include human foods and beverages such as soft drinks, candies, pastries, etc., foods for pets or livestock, chewing gums, etc. Such beverages, as distinguished from mere drinking water, typically contain a flavoring agent, a nutrient or sweetening agent, and optionally therapeutic agents. Chewing gums typically contain base materials, plasticizers or softeners, sugar or other suitable carbohydrates such as glucose, sorbitol, etc. Sugarless gums may contain other sweetening agents such as saccharin or sodium cyclamate. The ingredients of each of the foregoing oral compositions, other than said alkylenedioxy-bis(alkyl-propanedioic acid) compounds, as well as various mixtures of such ingredients are illustrative of carriers suitable for use in the oral cavity in accordance with the present invention.

The embodiments of this invention in which an exclusive property or privilege is claimed are defined as follows:

1. An oral composition effective in inhibiting formation of dental calculus, said composition comprising (1) an alkylenedioxybis(alkyl-propanedioic acid) compound selected from the group consisting of acids having the structural formula:

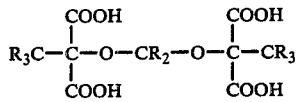

wherein R is hydrogen or lower alkyl and each R can be the same as or different from other R in said formula, and pharmaceutically acceptable salts of said acids and (2) a carrier suitable for use in the oral cavity, said compound being present in said composition in amount and concentration sufficient to substantially inhibit formation of dental calculus.

2. A composition according to claim 1 wherein said carrier comprises a dental polishing agent, flavoring agent, chewing gum base material, or human or animal food.

3. A composition according to claim 2 wherein at least one R in the —CR$_2$— radical is hydrogen and the number of carbon atoms in each of the two —CR$_3$ groups is not greater than 7.

4. A composition according to claim 3 selected from the group consisting of oral hygiene products and chewing gums.

5. A composition according to claim 3 wherein R is hydrogen, methyl or ethyl.

6. A composition according to claim 3 wherein each R in the —CR$_2$— radical is hydrogen.

7. A composition according to claim 3 wherein at least 2 R's in each of the two —CR$_3$ groups in said formula are hydrogen.

8. A composition according to claim 2 wherein each R in said formula is hydrogen.

9. A composition according to claim 8 selected from the group consisting of oral hygiene products.

10. A composition according to claim 8, said compound being selected from the group consisting of alkali metal and ammonium salts of said acids.

11. A composition according to claim 10 selected from the group consisting of foods and beverages to be ingested by humans or lower animals.

12. A composition according to claim 10 selected from the group consisting of mouth washes having a pH between about 4 and about 11, said concentration being between about 0.1% and about 3% by weight of said composition wherein said carrier comprises a flavoring agent.

13. A composition according to claim 10 selected from the group consisting of toothpastes having a pH between about 4 and about 11, said concentration being between about 0.1% and about 5% by weight of said composition wherein said carrier comprises a dental polishing agent or a flavoring agent.

14. A method for inhibiting formation of dental calculus which comprises introducing into an oral cavity containing exposed dental surfaces a composition according to claim 1.

15. A method for inhibiting formation of dental calculus which comprises introducing into an oral cavity containing exposed dental surfaces a composition according to claim 3.

16. A method for inhibiting formation of dental calculus which comprises introducing into an oral cavity containing exposed dental surfaces a composition according to claim 6.

17. A method for inhibiting formation of dental calculus which comprises introducing into an oral cavity containing exposed dental surfaces a composition according to claim 8.

* * * * *

UNITED STATES PATENT AND TRADEMARK OFFICE
CERTIFICATE OF CORRECTION

PATENT NO. : 4,143,125
DATED : March 6, 1979
INVENTOR(S) : David R. Dyroff, Walton F. Suchanek, Jr. and Thomas G. Schiff It is certified that error appears in the above-identified patent and that said Letters Patent are hereby corrected as shown below:

Front page, No. [75] Inventors: should read --- David R. Dyroff, Creve Coeur, Mo.; Walton F. Suchanek, Jr., Belleville, Ill. and Thomas G. Schiff, Clayton, Mo. ---.

Column 8, Claim 1, line 8, the line should read --- the same as or different from any other R in said formula, ---.

Signed and Sealed this

Fourth Day of September 1979

[SEAL]

Attest:

LUTRELLE F. PARKER

Attesting Officer     Acting Commissioner of Patents and Trademarks